(12) United States Patent
Ahvenniemi et al.

(10) Patent No.: US 7,932,922 B2
(45) Date of Patent: Apr. 26, 2011

(54) METHOD AND ARRANGEMENT IN TAIL THREADING OF A WEB FORMING MACHINE

(75) Inventors: Vesa Ahvenniemi, Helsinki (FI); Juha Laitio, Espoo (FI)

(73) Assignee: Metso Paper, Inc., Helsinki (FI)

(*) Notice: Subject to any disclaimer, the term of this patent is extended or adjusted under 35 U.S.C. 154(b) by 1370 days.

(21) Appl. No.: 10/595,978

(22) PCT Filed: Nov. 19, 2004

(86) PCT No.: PCT/FI2004/050168
§ 371 (c)(1),
(2), (4) Date: May 23, 2006

(87) PCT Pub. No.: WO2005/052251
PCT Pub. Date: Jun. 9, 2005

(65) Prior Publication Data
US 2009/0020581 A1   Jan. 22, 2009

(30) Foreign Application Priority Data
Nov. 26, 2003   (FI) ..................................... 20035221

(51) Int. Cl.
*H04N 7/18* (2006.01)
(52) U.S. Cl. ................. 348/88; 348/86; 348/92; 348/94
(58) Field of Classification Search ............... 348/86–95
See application file for complete search history.

(56) References Cited

U.S. PATENT DOCUMENTS

| 4,154,004 A | 5/1979 | Trötscher |
| 5,130,559 A * | 7/1992 | Leifeld et al. ............ 250/559.11 |

FOREIGN PATENT DOCUMENTS

| EP | 1 031 658 A2 | 8/2000 |
| EP | 1 335 067 A1 | 8/2003 |
| FI | 20035221 | 11/2003 |
| WO | 03/080928 A1 | 10/2003 |
| WO | 2005/052251 A1 | 6/2005 |

OTHER PUBLICATIONS

International Preliminary Report on Patentability issued in PCT/FI2004/050168.
International Search Report issued in PCT/FI2004/050168.
Search Report issued in priority application FI 20035221.

* cited by examiner

*Primary Examiner* — Andy S Rao
(74) *Attorney, Agent, or Firm* — Stiennon & Stiennon

(57) ABSTRACT

In a web-forming machine, a threading tail is formed from the web. The threading tail is transferred to the production section (10, 12-14) of the web-forming machine including a draw section (21). Monitoring takes place of both the formation of the threading tail and its transfer to the draw point (21). The holding point (24) and its environment that terminates the tail threading of the production section (10, 12-14) in question are additionally monitored, in order to detect the threading tail at the holding point (24) and thus to determine the success of the tail threading.

7 Claims, 3 Drawing Sheets

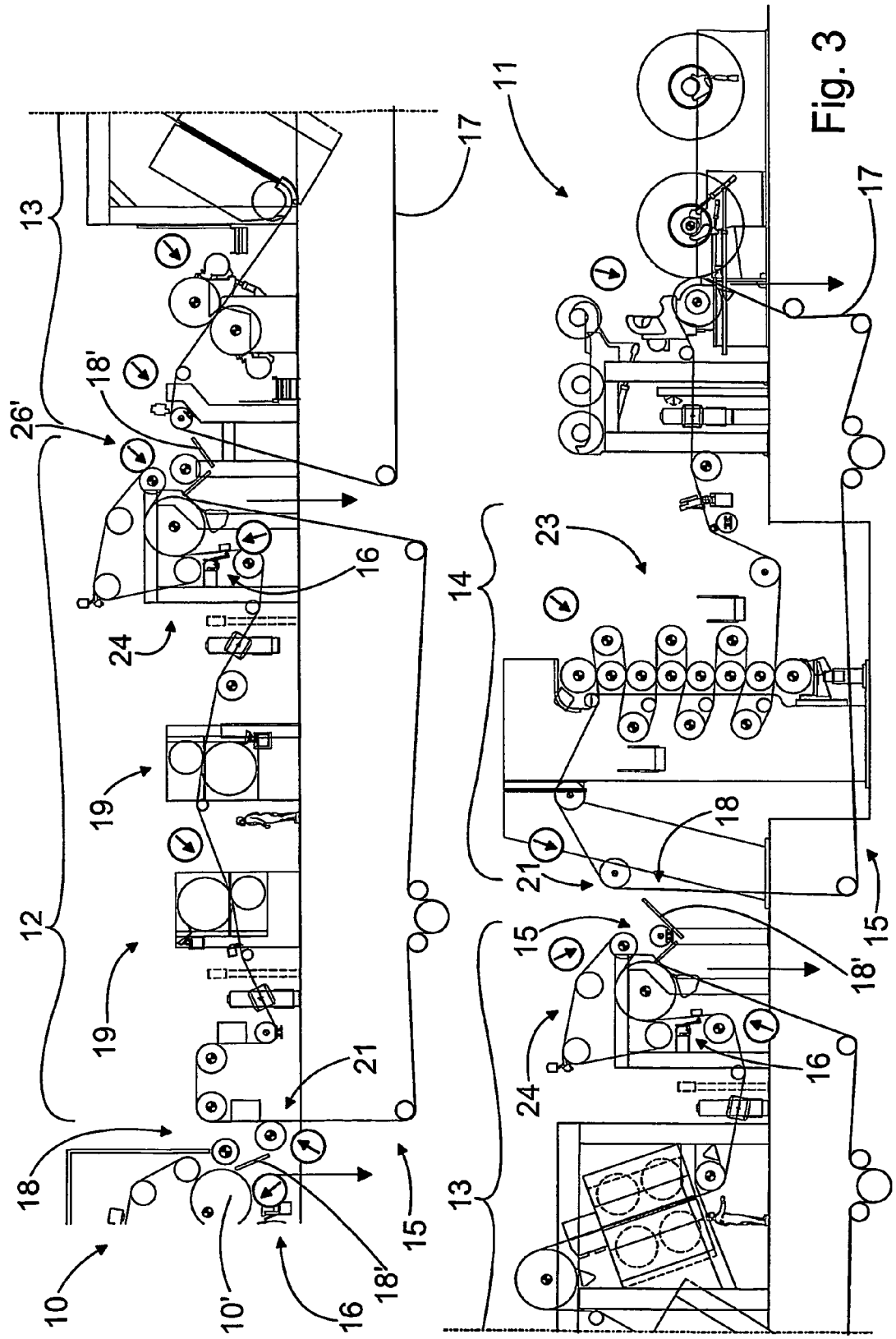

METHOD AND ARRANGEMENT IN TAIL THREADING OF A WEB FORMING MACHINE

CROSS REFERENCES TO RELATED APPLICATIONS

This application is a U.S. national stage application of international App. No. PCT/FI2004/050168, filed Nov. 19, 2004, the disclosure of which is incorporated by reference herein, and claims priority on Finnish App. No. 20035221, filed Nov. 26, 2003.

STATEMENT AS TO RIGHTS TO INVENTIONS MADE UNDER FEDERALLY SPONSORED RESEARCH AND DEVELOPMENT

Not applicable.

BACKGROUND OF THE INVENTION

The present invention relates to a method in the tail threading of a web-forming machine, in which a threading tail is formed from the web, and is transferred to the production section of a web-forming machine including a draw point, and in which method monitoring takes place of both the formation of the threading tail and its transfer to the draw point, which is at the start of the said production section, and from which the threading tail is pulled in the tail threading towards a holding point at the end of the production section. The invention also relates to a corresponding arrangement in the tail threading of a web-forming machine.

European patent application number 1335067 discloses a method and arrangement in transferring the web from one production section of a paper machine to another. In the tail threading, a threading tail, which is cut from the web, is used in the tail threading. According to the application, the forming of the threading tail is monitored, for example, using camera. If something abnormal occurs in the threading tail or in the path of its travel, the formation of the threading tail, or its transfer to the next production section, are adjusted using the control system. For example, on the basis of a detected deviation, water cutting can be adjusted, either manually, or automatically.

The arrangement is intended for monitoring and controlling the formation of a threading tail between production sections. The camera can also be used to determine the failure of the tail threading of the threading tail to the roll nip, forming the draw point in the following production section. Problems arising after the point in question will, however, remain unnoticed. In addition, the automatic control disclosed is usually impossible, if formation of the threading tail fails completely. This is because, at present production speeds, only a moment is needed for commencing tail threading. If tail threading fails immediately when it starts, it will thus be impossible to use software to control its formation. In other words, the method and apparatus disclosed can only be used to monitor one part of the tail threading. Despite the numerous adjustment possibilities, adjustment is often also impossible in practice, as tail threading takes a maximum of a few seconds. In addition, monitoring both before and during tail threading leads to long imaging times, which require an accurate camera and powerful peripheral devices. Despite the versatile equipment, it is impossible to use the arrangement to determine whether the tail threading has succeeded, never mind determining the problem points that caused it to fail.

SUMMARY OF THE INVENTION

The invention is intended to create a new method in tail threading in a web-forming machine, by means of which it will be possible not only to determine whether tail threading has succeeded, but also to locate the problem areas. In addition, the invention is intended to create a new arrangement in tail threading in a web-forming machine, which is easier than before to use, but which can be utilized more comprehensively than previously. According to the invention, the tail threading is monitored over the entire length of the production section, particularly at its critical points. In addition, the forming of the threading tail is monitored in the preceding production section. The use of the method provides definite information on the success of the tail threading. In problem cases on the other hand, the problem points can be located rapidly. The method is also suitable for application in separate tail-threading systems. The arrangement according to the invention is easy to bring into use and is preferably connected to the machine-control system of the web-forming machine. On the basis of the observations obtained using the arrangement, it will then be possible to adjust the formation of the threading tail and its tail threading to the production section. In addition, the system can also be used to detect other problems arising from the web-forming machine or its auxiliary devices.

In the following, the invention is examined in detail with reference to the accompanying drawings, depicting some applications of the invention.

BRIEF DESCRIPTION OF THE DRAWINGS

FIG. 3 shows the arrangement according to the invention fitted in connection with the finishing section of a second web-forming machine.

DESCRIPTION OF THE PREFERRED EMBODIMENTS

Figure 1:
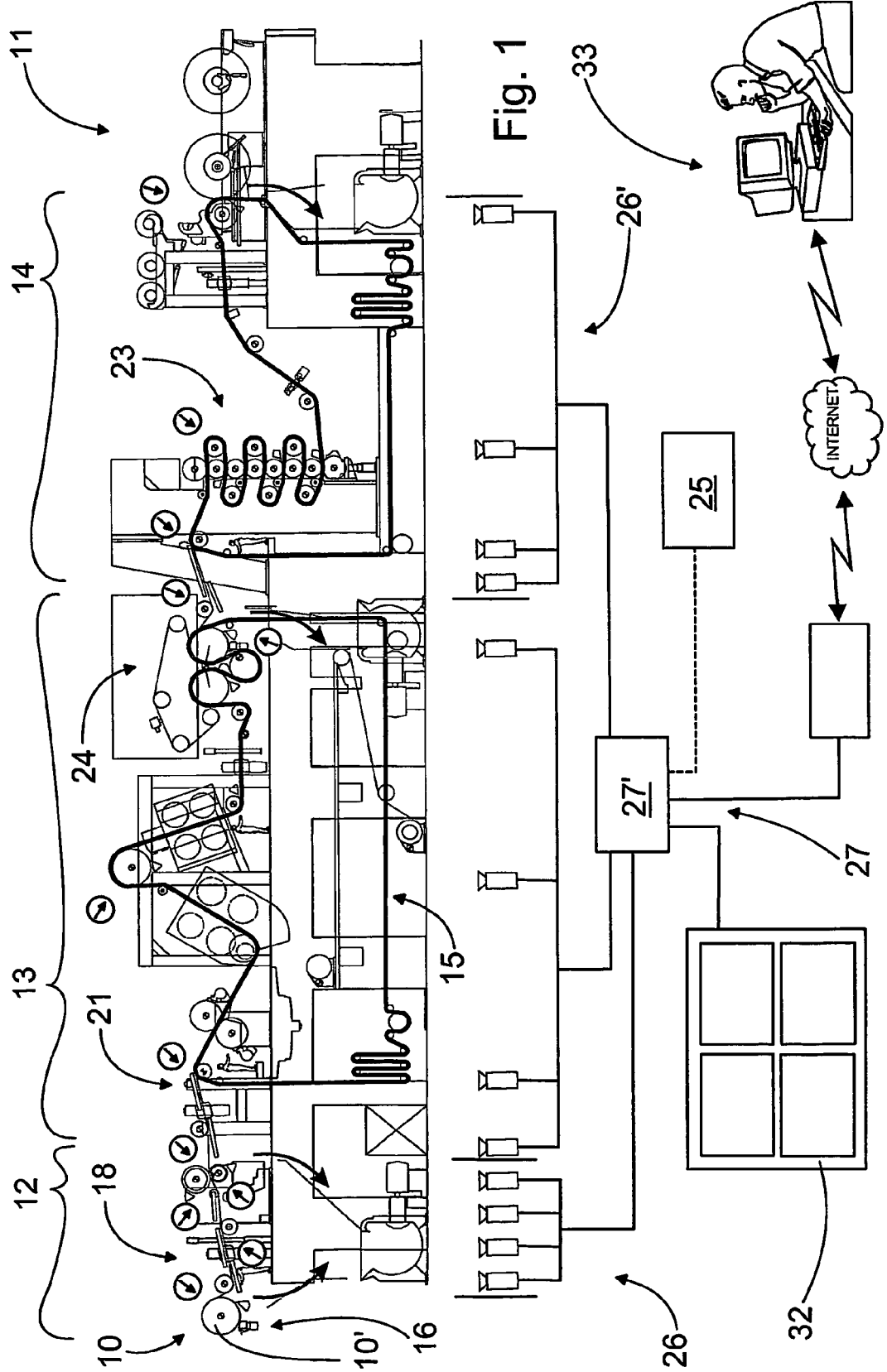
FIG. 1 shows a schematic diagram of the arrangement according to the invention fitted in connection with the finishing section of a web-forming machine.

FIG. 1 shows the finishing section of one web-forming machine. Web-forming machines are usually paper or board machines. Only the final drying cylinder 10', against which the threading tail is cut, of the dryer section 10 of the web-forming machine is visible at the left-hand side of FIG. 1. Generally in tail threading, a threading tail is first formed from the web, and is transferred to the production section of the web-forming machine forming the draw point. The sequential production sections in FIG. 1 show not only the dryer section 10, but also pre-calendering 12, coating 13, and calendering 14, after which the finished web is reeled on a reeler 11. In this application, the case is thus of so-called online finishing, in which the web is guided from the dryer section directly to the finishing, without intermediate reeling. To minimize production losses, the tail threading particularly of finishing, which contains quite many discontinuity points, must function smoothly. Of course, the method according to the invention can be applied elsewhere than in the production stages relating to finishing, as well as in so-called offline finishing processing.

In the method, the formation of the threading tail and its transfer to the draw point 21 (FIG. 2) are monitored. The draw point is at the start of the production section and from the draw point the threading tail is drawn in the tail threading to a holding point 24 at the end of the production section. According to the invention, the holding point 24, which terminates the tail threading of the production section in question, and its environment are also monitored, in order to determine the success of the tail threading. Thus definite information on the success of the tail threading is obtained, after which the formation of a threading tail and its transfer to the following section can be started. For tail threading, the web-forming machine includes cutting devices 16, arranged in connection with the first of the sequential production sections, which are intended for cutting the threading tail from the web formed on the web-forming machine. Correspondingly, the second production section has threading devices 15, for threading the threading tail through the production section in question. In practice, the threading devices 15 form a draw point 21 at the start of the second production section. Further, the web-forming machine includes transfer devices 18 between the production sections, for transferring the threading tail formed in the first production section to the threading devices 15 of the second production section. Thus, the transfer devices are used to transfer the threading tail to the threading devices 15 of the second production section, which extend to the holding point at the end of the second production section. When the threading tail has been taken through the production section to the holding point by the threading devices, tail threading has been completed in the production section in question. The web-forming machine also includes control equipment for controlling the aforementioned devices, which devices and operation are described later in greater detail.

Correspondingly, the arrangement includes camera devices 26 between the production sections, in order to monitor the formation of the threading tail and its transfer to the draw point 21. In addition, there are memory devices 27 for storing the image information imaged using the camera devices 26 and displaying it in a desired manner. According to the invention, camera devices 26' are also arranged in connection with the holding point 24, in order to determine the success of the tail threading, at which holding point 24 the tail threading of the second production section terminates. Thus, besides ensuring the formation of the threading tail and its transfer, it is also possible to ensure the arrival of the threading tail at the holding point, when the tail threading of the production section will have succeeded.

According to the invention, the formation and transfer of the threading tail and the holding point 24 are monitored separately. For this purpose the camera devices 26 and 26' include three cameras 28, 29 and 30, shown in FIG. 2. The first camera 28 is arranged in connection with the cutting devices 16 and the second camera 29 in connection with the draw point 21. This makes it possible to ensure the success of the formation and transfer of the threading tail. Correspondingly, the third camera 30 is arranged in connection with the holding point 24, so that the presence of the threading tail at the end of the production section can be detected. Thus in practice it is easy to monitor the most critical points in the production section.

Image information on a successful tail threading is also stored, and can be exploited to define good settings. However, the arrangement is particularly needed in problem situations, in which the tail threading fails for some reason. Thus in the method, some other selected point is additionally monitored in the relevant production section of the web-forming machine. For this purpose, the camera devices 26 and 26' also include a fourth camera 31, which is arranged to be installed at a selected point in the relevant production section of the web-forming machine. The fourth point to be monitored is preferably chosen on the basis of the information obtained using the other cameras. According to the method, the tail threading is monitored by imaging different points and the information obtained in the imaging is stored and is displayed synchronized with a particular point in the threading tail. Thus, a single glance will be enough to determine that the threading tail is progressing through the production section. On the basis of the capacity of the devices available, the image information must generally be stored before it is displayed. Of course, using modern powerful devices, the information may be displayed in real time during its storing, which will accelerate the solution of problems.

In any event, tail threading is a process of short duration, the real-time viewing of image information on which will provide only little information. From the image information, it is mainly possible only to decide whether or not the tail threading has succeeded. In other words, in practice the entire tail threading sequence is always run through, after which the control values of the various devices can be altered. Thus, if deviations appear in the tail threading, the location of the problem point is determined on the basis of the image information stored during the monitoring. According to the invention, the location of the problem point is determined from the time-specific image information, on the basis of the calculated rate of progression of the threading tail. In practice, the transfer devices generally operate reliably, so that the problem points are usually in the threading devices. The threading tail then moves to the draw point, pulled by the threading devices. When the threading tail breaks, it suddenly slackens, which can be seen when monitoring the draw point. In other words, in the time between the breaking and the transferring to the draw point, the threading tail will have progressed in the production section at the speed of the threading devices, which is known, or which can be easily determined. At the same time, the geometry of the production section is known, on the basis of which the route traveled by the threading tail can be determined. Thus, using the time of progression of the threading tail, combined with the geometry of the production section, the problem point can be determined with great precision. In other words, the progression journey of the threading tail is adapted to the following production section of the web-forming machine.

Figure 2:
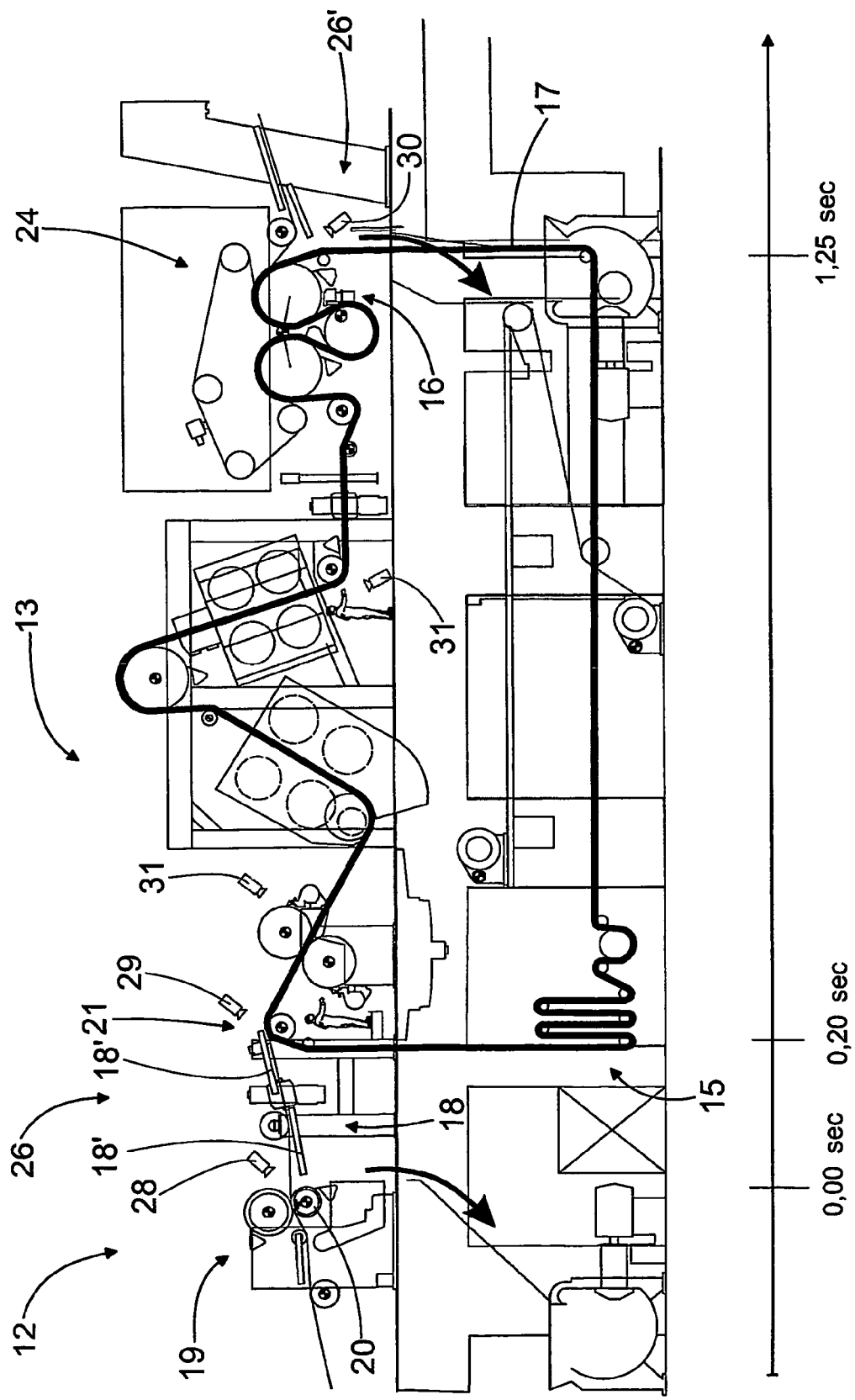
FIG. 2 shows a partial enlargement of the web-forming machine of FIG. 1.

In FIG. 2, a time line is added, which shows the location of the threading tail as a function of the progression time. The time line is specific for each geometry and is also affected by the speed of the threading devices. Each camera records the time at which the tail threading started and the time at which a change took place in the state of the camera. On the basis of the image information of the cameras it is thus possible to determine how far the threading tail progressed in the production section before the break. The location of the problem point can thus easily be established from the graph according to FIG. 2. The graph can also be in the memory devices, in which case changes made in the settings will be updated to the time line. The graph can also be output on an array at the web-forming machine, on which there can also be time lines for different production speeds.

The cause of the problem can be found by examining visually the point determined on the basis of the image information. If the problem remains undefined, the fourth camera according to the invention is set at the point in question and tail threading is attempted again. The camera can be located even in difficult places and can be used even during tail threading. In addition, the image information can be processed, for example, by enlarging the image or by slowing it, which will facilitate the determining of the problem. Once the cause of the problem has been found, the fault can be easily repaired. In addition, the tail threading can be adjusted, by using the control apparatus 25, which is usually the web-forming machine's machine-control system (FIG. 1). In practice, the tail threading sequence is run always from start to finish. In other words, during a single program cycle the control of the various devices are connected to and interlocked with each other, so that rapid operations can be controlled precisely. In practice, the adjustment of the devices during tail threading is thus impossible. However, the control values can be altered between tail threading attempts and the equipment otherwise serviced or repaired.

FIG. 1 shows schematically the configuration of the arrangement. According to the invention, the memory devices 27 of the camera devices 26 and 26' are connected to the control apparatus 25, in order to combine the properties of the web-forming machine with the image information. Thus, in practice the geometry, production settings, and web grade of the production section are included in the image information being stored. A successful tail threading and the associated settings can thus be utilized later when setting up a good tail threading. In other words, suitable default values can be predefined for a specific web grade, for example, when changing the grade or when starting up a new production section.

Usually, the memory devices 27 consist of a computer 27', which includes devices for processing and storing image information. In addition, a display device 32 is connected to the computer 27' and preferably shows the image information of all the cameras, synchronized at the same point in the threading tail. In addition, according to the invention the camera devices of the various production sections of the web-forming machine are connected to the memory devices arranged as a single totality. In other words, a single system can be used to store the image information of each production section, which can then be processed and examined during or after the tail threading of each production section. This simplifies the arrangement and reduces costs. The memory devices 27 can also be connected, for example, over the Internet to a remote tool 33, so that the monitoring and problem-solving of the tail threading can take place as a remote operation.

In the following, one production section is examined in greater detail with reference to FIG. 2, which shows the coating 13 forming part of the finishing section shown in FIG. 1. In this case, three cameras 28-30 are used, which are located according to the criteria described above. The coating in question is preceded by pre-calendering 12. From the pre-calender 19, the threading tail is led down to broke processing. The first camera 28 is used to monitor the detaching of the threading tail from the roll 20 of the pre-calender 19. The detached threading tail is transferred toward the coating 13 using transfer devices 18, which in this case are formed by two consecutive vacuum belt conveyors 18'. The transfer devices 18 are used to transfer the threading tail to the threading devices 15, which form the draw point 21. In this case, the transfer devices 15 are formed of rope threaders 17, which form a rope nip at the start of the coating 13. In practice, the threading tail progresses between the rope threaders 17. The threading tail is fed at a slight angle to the rope nip, so that only the first part of the threading tail travels in the rope threaders, the rest of it coming more to the center of the web-forming machine. At the rope nip, there is a second camera 29 according to the invention, on the basis of the image information of which it is known exactly when the threading tail transfers to the threading devices 15. The threading devices 15 pull the threading tail to the holding point 24 at the end of the coating 13, where the threading tail is run down to broke processing. A third camera 30 according to the invention is arranged in connection with the holding point 24, and can thus be used to detect the success of the tail threading in the production section in question, i.e. in this case in the coating 13.

In problem situations, such as when the threading tail breaks in the middle of tail threading, the problem will be detected particularly by the first or second camera, when the threading tail suddenly slackens. On the other hand, when the properties of the web-forming machine are known, the time taken for tail threading in the production section in question will also be known, so that it will be known when the third camera should detect the threading tail. In practice, in the time between entry to the draw point and breaking the threading tail will have thus progressed at a specific speed over a specific distance, it being possible to determine the time that has elapsed for this, on the basis of the image information obtained using the cameras. In addition, when the structure of the web-forming machine is known, it will be possible to determine the probable location of the break. That is, the point reached by the threading tail in the aforementioned time. The point in question is examined, and maintenance and adjustments are carried out if necessary. If the problem remains undetermined in a visual examination, a fourth camera according to the invention is placed at the problem location. For example, the cause of the problem will soon be seen from a precise slow-motion rerun image. If necessary, the fourth camera can be moved, or even several cameras can be used. FIG. 2 shows two examples of locations for the fourth camera 31. In coating, the critical points are the coating station and the contactless dryer. The distance determined on the basis of the time of the progression of the threading tail can also be calculated backwards from the holding point, which will make the definition of the problem point even more exact. In FIGS. 1 and 3, the locations of the cameras 28-31 are shown by arrows in circles.

FIG. 3 shows the arrangement according to the invention arranged in another kind of finishing section. The same reference numbers are used for components that are functionally similar. The arrows facing downwards are used here too to depict the threading tail and the entire web being directed downwards to broke processing. In the finishing sections 12-14 of FIG. 3 too rope threaders 17 are used as the threading devices 15 and vacuum belt conveyors 18' as the transfer devices 18. In this case, a single-contact holding point 24 is used, so that the difference in speed between the threading devices 15 and the holding point 24 will not interfere with the tail threading, thus making tail threading even more reliable.

The arrangement according to the invention can be simply and rapidly introduced in a mill, even as a retrofit. If necessary, training is arranged beforehand and default settings are used. In practice, the arrangement can even be sold separately as a tail-threading product, independently of the machine-control system. The arrangement is mainly intended for the automatic imaging of tail threading attempts, in which case the cameras are installed permanently in the web-forming machine. The signal for commencing imaging is obtained, for example, from the control of the threading devices. On the other hand, the real-time image information of the cameras can be used to monitor the production sections, without storing, which is commenced when the tail threading is started. For example, starting the first tail threading blowing in the production section will also start the monitoring. In other words, the arrangement is connected to the tail threading sequence of the web-forming machine, so that storing is automatic. In practice, the image information stored from the tail threading attempts can be viewed easily and rapidly. Each tail threading attempt is stored as its own file and all the cameras can be rapidly viewed synchronized simultaneously. The image information can be further stored in different file formats in different storage media, or even be transferred outside the mill for analysis.

Already now it is in practice possible to view all four cameras simultaneously during imaging. As cameras continue to develop even higher imaging speeds and longer storing times will be achieved. On the other hand, increases in memory capacity will also permit the number of cameras to be increased up to eight or even twelve cameras. In practice, the image information always includes the imaging time. If desired, the reason for the imaging can also be recorded, this being, for example, starting originating from the machine control, or starting due to a break, or a manual start. As tail threading is a very rapid process, an imaging time of five seconds from an external signal will be sufficient in practice. Even at most, the time for tail threading nowadays is about two seconds.

Each camera in the arrangement is a digital camera, preferably a digital high-speed camera. Due to the demanding conditions, the cameras are encased and a connection for compressed-air cooling. Modern cameras can, however, be used without a case, at least at the dry end of the web-forming machine. Pattern recognition can also be arranged in the cameras, which will assist in monitoring the threading tail. In practice, the cameras are connected by leads to memory devices, although wireless technologies can also be used. Particularly the moveable, i.e. the fourth cameras are preferably wireless, so that they can be easily and quickly put in different locations. The cameras used can be of nearly any kind at all. For example, a camera manufactured by Ikegami has a sensitivity of 0.02 lux at $f_1$ and can be used to take 50 half images in a camera segment. In practice, full-resolution, double-speed, and thermal cameras are also possible.

The invention claimed is:

1. An arrangement for tail threading in a web-forming machine, comprising:
    a plurality of sequential production sections;
    a first production section of the plurality of sequential production sections having a cutting device which cuts a threading tail from the web being formed on the web-forming machine;
    a second production section of the plurality of sequential production sections following in sequence the first production section, the second production section having a start, and a threading device arranged to thread a tail through the second production section, which threading device having a first draw point at the start of the second production section;
    a transfer device arranged to transfer a threading tail from the first production section to the threading device of the second production section;
    wherein the second production section has an end which defines a holding point, to which the threading device extends;
    control equipment arranged in controlling connection to the cutting device, the transfer device, and the threading device;
    a first camera device arranged for collecting time-specific image information of formation of a threading tail by the cutting device;
    a second camera device arranged for collecting time-specific image information of a web tail in the transfer device at the first draw point;
    a third camera device arranged for collecting time-specific image information of the holding point; and
    memory devices connected in image storing relation to the first camera device, the second camera device, and the third camera device for storing time-specific image information collected using the first camera device, the second camera device and the third camera device, the memory devices connected to a display device such that images captured by the first camera device, the second camera device and the third camera device can be displayed in a selected manner.

2. The apparatus of claim 1 further comprising a fourth camera device arranged for collecting time-specific image information of a selected point in the plurality of sequential production sections, the fourth camera device connected in time-specific image information supplying relation to the memory devices, the memory devices connected to the display device such that images captured by the fourth camera device can be displayed in a selected manner.

3. The apparatus of claim 2, wherein the memory devices are connected to the control equipment so as to combine the properties of the production section of the web-forming machine and the image information.

4. The apparatus of claim 1, wherein the first camera device, the second camera device, and the third camera device are connected to the memory devices arranged as a single system which stores the time-specific image information of each of the first camera device, the second camera device, and the third camera device, so that such time-specific image information can be processed and examined during or after a tail threading of each sequential production section.

5. The apparatus of claim 1, wherein each of the first camera device, the second camera device, and the third camera is a digital high-speed camera.

6. A method of tail threading in a web-forming machine of a selected geometry and a selected web speed therethrough; the method comprising the steps of:
    forming a threading tail from a web;
    imaging to form first images the formation of the threading tail with a first camera and storing with a time reference said first images, the first camera recording a tail threading start time and each time at which a change takes place in the first images;
    transferring the tail to a production section of the web-forming machine, the production section having a start and an end, the transferring taking place at a draw point which is at the start of the production section;
    imaging to form second images with a camera the transfer of the threading tail to the draw point at the start of the production section and storing with a time reference said second images, the second camera recording the tail threading start time and each time at which a change takes place in the second images;
    pulling the threading tail toward a holding point at the end of the production section;
    imaging to form third images of the holding point and its environment and storing with a time reference said third images, the third camera recording the tail threading start time and each time at which a change takes place in the third images;
    determining a time line of locations of the threading tail as a function of time based on the selected geometry and the selected speed of progress through the web-forming machine;
    determining a location of a problem point by detecting a time of slacking of the tail at the draw point in the images from the second camera; and
    using the time line to calculate the problem point location.

7. The method of claim 6, wherein an additional selected point of the production section of the web-forming machine is imaged.

* * * * *